United States Patent
Sharratt et al.

(10) Patent No.: US 11,007,471 B2
(45) Date of Patent: *May 18, 2021

(54) PROCESS FOR PURIFYING (HYDRO)FLUOROPROPENES CONTAMINATED WITH HALOGENATED ETHANE

(71) Applicant: MEXICHEM FLUOR S.A. DE C.V., San Luis Potosi C.P. (MX)

(72) Inventors: Andrew Sharratt, Cheshire (GB); Robert Low, Cheshire (GB)

(73) Assignee: MEXICHEM FLUOR S.A. DE C.V., Tlalnepantla (MX)

( * ) Notice: Subject to any disclaimer, the term of this patent is extended or adjusted under 35 U.S.C. 154(b) by 0 days.

This patent is subject to a terminal disclaimer.

(21) Appl. No.: 16/588,802

(22) Filed: Sep. 30, 2019

(65) Prior Publication Data
US 2020/0038800 A1 Feb. 6, 2020

Related U.S. Application Data

(62) Division of application No. 15/316,978, filed as application No. PCT/GB2015/051671 on Jun. 9, 2015, now Pat. No. 10,456,730.

(30) Foreign Application Priority Data

Jun. 9, 2014 (GB) ..................................... 1410174

(51) Int. Cl.
*B01D 53/04* (2006.01)
*C07C 17/389* (2006.01)
(Continued)

(52) U.S. Cl.
CPC ......... *B01D 53/0438* (2013.01); *B01D 53/02* (2013.01); *B01D 53/04* (2013.01);
(Continued)

(58) Field of Classification Search
CPC .... B01D 53/0438; B01D 53/02; B01D 53/04; B01D 2257/206; B01D 2257/80;
(Continued)

(56) References Cited

U.S. PATENT DOCUMENTS 3,446,645 A 5/1969 Drost
3,625,866 A 12/1971 Conde
(Continued)

FOREIGN PATENT DOCUMENTS

CN 1827566 9/2006
CN 101012146 8/2007
(Continued)

OTHER PUBLICATIONS

CFCs, The Day after, International Institute of Refrigeration, Sep. 1994.
(Continued)

*Primary Examiner* — Emmanuel E Duke
(74) *Attorney, Agent, or Firm* — Brinks Gilson & Lione; Yuezhong Feng

(57) ABSTRACT

A process for treating a composition comprising one or more desired (hydro)fluoroolefins and one or more undesired halogenated ethanes, halogenated methanes or mixtures thereof so as to reduce the concentration of at least one undesired halogenated ethane or halogenated methane, the process comprising contacting the composition with an adsorbent comprising pores having openings which have a size across their largest dimension of about 6 Å or less.

28 Claims, 1 Drawing Sheet

(51) Int. Cl.
  *F25B 43/00* (2006.01)
  *C09K 5/04* (2006.01)
  *B01D 53/02* (2006.01)
  *C07C 17/38* (2006.01)
  *C07C 17/383* (2006.01)

(52) U.S. Cl.
  CPC ............ *C07C 17/38* (2013.01); *C07C 17/383* (2013.01); *C07C 17/389* (2013.01); *C09K 5/045* (2013.01); *F25B 43/003* (2013.01); *B01D 2253/108* (2013.01); *B01D 2253/308* (2013.01); *B01D 2256/26* (2013.01); *B01D 2257/206* (2013.01); *B01D 2257/2066* (2013.01); *B01D 2257/80* (2013.01); *B01D 2259/402* (2013.01); *B01D 2259/4009* (2013.01); *C09K 2205/126* (2013.01); *Y02C 20/30* (2013.01); *Y02P 20/151* (2015.11)

(58) Field of Classification Search
  CPC ........ B01D 2259/402; B01D 2253/108; B01D 2253/308; B01D 2256/26; B01D 2257/2066; B01D 2259/4009; C10L 229/0542; C07C 17/38; C07C 17/383; C07C 17/389; C09K 5/045; C09K 2205/126; F25B 43/003; Y02P 20/151; Y02C 20/30; B01J 20/18
  See application file for complete search history.

(56) References Cited

U.S. PATENT DOCUMENTS

| | | | |
|---|---|---|---|
| 3,865,887 A | 2/1975 | Gordon | |
| 4,906,796 A * | 3/1990 | Yates | C07C 17/389 570/179 |
| 4,940,824 A | 7/1990 | Yates | |
| 5,164,355 A | 11/1992 | Farris et al. | |
| 5,233,107 A | 8/1993 | Jansen | |
| 5,288,930 A * | 2/1994 | Shields | C07C 17/389 570/179 |
| 5,396,001 A | 3/1995 | Pennetreau | |
| 5,454,966 A | 10/1995 | Thomas et al. | |
| 5,514,633 A | 5/1996 | Noguchi et al. | |
| 5,523,499 A | 6/1996 | Corbin et al. | |
| 5,536,891 A | 7/1996 | Beard, Jr. | |
| 5,575,833 A | 11/1996 | Griffin | |
| 5,742,066 A | 4/1998 | Cavestri | |
| 5,910,161 A | 6/1999 | Fujita et al. | |
| 6,313,059 B1 | 11/2001 | Lavin et al. | |
| 6,403,847 B1 | 6/2002 | Nakada et al. | |
| 6,589,444 B2 | 7/2003 | Thomas et al. | |
| 7,041,264 B2 | 5/2006 | Horiba et al. | |
| 7,084,316 B2 | 8/2006 | Ohno et al. | |
| 7,094,935 B2 | 8/2006 | Suzuki et al. | |
| 7,384,519 B2 | 6/2008 | Cottrell et al. | |
| 2003/0157009 A1 * | 8/2003 | Corr | C07C 17/389 423/240 S |
| 2004/0089839 A1 | 5/2004 | Thomas et al. | |
| 2004/0119047 A1 | 6/2004 | Singh et al. | |
| 2005/0124834 A1 | 6/2005 | Ohno et al. | |
| 2005/0133360 A1 | 6/2005 | Cottrell et al. | |
| 2006/0043331 A1 | 3/2006 | Shankland et al. | |
| 2007/0015944 A1 * | 1/2007 | Hoos | B01J 20/28078 570/262 |
| 2008/0011159 A1 | 1/2008 | Thomas et al. | |
| 2008/0098755 A1 | 5/2008 | Singh et al. | |
| 2010/0162738 A1 * | 7/2010 | Low | C07C 17/389 62/101 |
| 2011/0105809 A1 * | 5/2011 | Devic | C07C 17/389 570/179 |
| 2011/0152586 A1 * | 6/2011 | Low | C07C 17/354 570/175 |
| 2012/0010594 A1 | 1/2012 | Holt et al. | |
| 2012/0203037 A1 * | 8/2012 | Sharratt | C07C 17/389 570/179 |
| 2012/0256120 A1 * | 10/2012 | Bouvier | C10M 175/0091 252/68 |
| 2012/0266750 A1 | 10/2012 | Hilton et al. | |
| 2014/0051896 A1 * | 2/2014 | Imura | C07C 21/18 570/179 |
| 2014/0275650 A1 * | 9/2014 | Kopkalli | C07C 17/202 570/160 |
| 2016/0060192 A1 * | 3/2016 | Sharratt | C07C 17/389 424/45 |
| 2016/0060291 A1 | 3/2016 | Sharratt et al. | |

FOREIGN PATENT DOCUMENTS

| | | |
|---|---|---|
| CN | 102101822 | 6/2011 |
| CN | 102101823 | 6/2011 |
| EP | 0974633 A1 | 1/2000 |
| EP | 1116706 A1 | 7/2001 |
| EP | 1116706 B1 | 12/2004 |
| JP | 10443346 A | 2/1989 |
| JP | 03072437 | 3/1991 |
| JP | H4110388 | 4/1992 |
| JP | 6327968 A | 11/1994 |
| JP | 1997 241189 | 9/1997 |
| JP | H09241189 A | 9/1997 |
| JP | 11293273 A | 10/1999 |
| JP | 2000-39235 A | 2/2000 |
| JP | 2001 523561 A | 11/2001 |
| JP | 2003 533447 A | 11/2003 |
| JP | 2004 339187 A | 12/2004 |
| JP | 2010-083818 A | 4/2010 |
| KR | 0159176 | 1/1999 |
| WO | WO 98/19982 A1 | 5/1998 |
| WO | WO 99/26708 A1 | 6/1999 |
| WO | WO 2001/017646 A1 | 3/2001 |
| WO | WO 2001/83411 A1 | 11/2001 |
| WO | WO 2004/037913 A2 | 5/2004 |
| WO | WO 2004/052264 A1 | 6/2004 |
| WO | WO 2004/074225 A1 | 9/2004 |
| WO | WO 2005/042451 A2 | 5/2005 |
| WO | WO 2005/044765 A2 | 5/2005 |
| WO | WO 2005/067554 A2 | 7/2005 |
| WO | WO 2005/103191 A2 | 11/2005 |
| WO | WO 2007/002625 A2 | 1/2007 |
| WO | WO 2007/053697 A2 | 5/2007 |
| WO | WO 2007/144632 A1 | 12/2007 |
| WO | WO 2008/008695 A1 | 1/2008 |
| WO | WO 2010/059685 | 5/2010 |
| WO | WO 2011/045559 A1 | 4/2011 |
| WO | WO 2013/151070 A1 | 10/2013 |

OTHER PUBLICATIONS

Dyer, An Introduction to Zeolite Molecular Sieves, John Wiley & Sons Ltd, pp. 93-97 and 102-106, 1988.
English translation of Extract from chapter 2 of French Oil Institute publication, 4 pages, 1998.
Falcon (Material Safety Data Sheet 152a; Oct. 30, 2006; pp. 1-5).
Foley, H., "Carbogenic molecular sieves: synthesis, properties and applications." Microporous Materials, 4, 1995, 407-433.
Green, Introducing . . . Carbon Molecular Sieve, http://hengyeusa.com, printed Nov. 2, 2013.
Henne et al., "Fluorinated Derivatives of Propane and Propylene." American Chemical Society, Mar. 1946, vol. 68, pp. 496-497.
International Preliminary Report on Patentability for PCT/GB2007/00223 dated Dec. 16, 2008.
International Search Report and Written Opinion for International Application No. PCT/GB2015/051671, dated Oct. 2, 2015 (11 pages).
Kawahira, M. Japanese Association of Refrigeration, 1981, pp. 188-191 (Partial English translation).
Koresh et al., "Study of Molecular Sieve Carbons." J.C.S. Faraday I, 76, 1980, 24722484.
Lautensack et al., Molecular Sieve a refrigerant desiccant, Refrigerating Engineering, 33-36, May 1957.

(56) References Cited

OTHER PUBLICATIONS

Lemus et al., "Removal of chlorinated organic volatile compounds by gas phase adsorption with activated carbon." Chemical Engineering Journal, 211-212, 2012, 246253.
Mariwala et al., "Adsorption of halocarbons on a carbon molecular sieve." Microporous and Mesoporous Materials, 22, 1998, 281-288.
Mieville et al., Carbon Molecular Sieves and Other Porous Carbons, Mega-Carbon Company, downloaded from citeseerx.ist.psu.edu, on Mar. 14, 2016.
Molecular Sieve Desiccant, Ford Motor Company Engineering Material Specification, Aug. 14, 2002, 4 pages.
Pfenninger, Manufacture and Use of Zeolites for Adsorption Processes, in Molecular Sieves: Science and Technology, vol. 2, 163-198, 1998.
Raabe, G., "A Force Field for 3,3,3-Fluoro-1-propenes, Including HFO-1234yf" J. Phys. Chem. B, 114, 2010, 10133-10142, Abstract.
Raabe, G., "Molecular Modeling of Fluoropropene Refrigerants" J. Phys. Chem. B, 116, 2012, 5744-5751.
Reid et al., "Adsorption Kinetics and Size Exclusion Properties of Probe Molecules . . . " J. Phys. Chem. B, 105, 2001, 10619-10628.
UK Search Report issued on GB Application No. 1307327.5 dated Dec. 18, 2013.
Union Carbide Molecular Sieves, Automotive Air Conditioning Desiccants, technical brochure, 1986.
UOP LLC, "AW-500 Molsiv™ Adsorbent," XP002744594, Retrieved from http://www.psbindustries.com/pdf/UOP%20Type%20AW-500%20Data%20Sheet.pdf, Dec. 31, 2001 (1 page).
UOP Molecular Sieves, technical brochure, 1988.
UOP, Handling of zeolite molecular sieve adsorbents in process units, technical brochure, 2009.
Vaduva et al., "Carbon Molecular Sieves Production and Performance Assessment in $CO_2$ Separation by Selective Absorption." U.P.B. Sci. Bull., Series B, 69(3), 2007, 95-106.
Written Opinion of the International Searching Authority; PCT/GB2014/051259 dated Apr. 23, 2014.

\* cited by examiner

Figure 1: Refrigerant adsorption
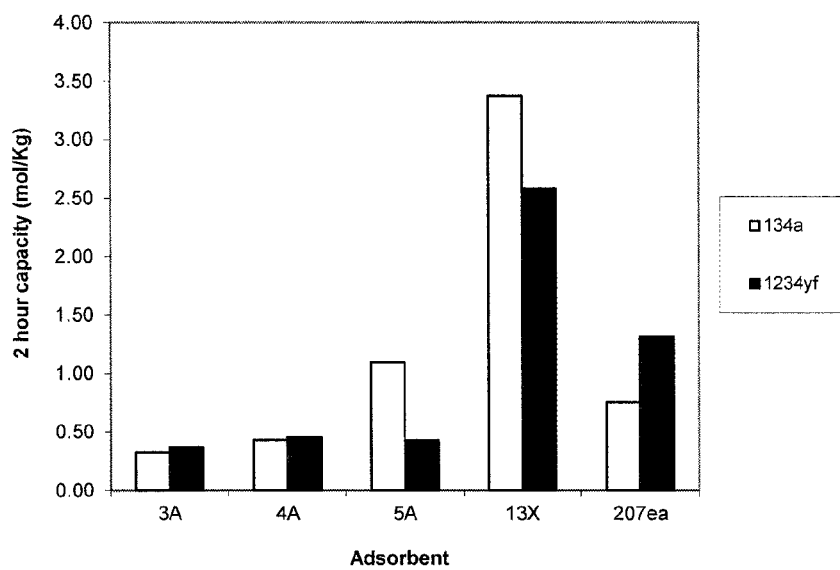
Figure 2: Refrigerant adsorption
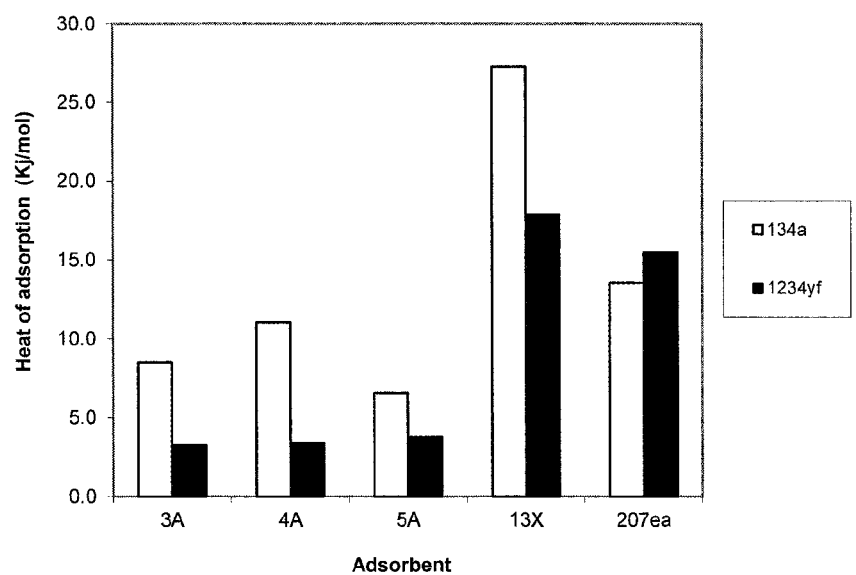

PROCESS FOR PURIFYING (HYDRO)FLUOROPROPENES CONTAMINATED WITH HALOGENATED ETHANE

CROSS-REFERENCE TO RELATED APPLICATIONS

This application is a divisional of U.S. application Ser. No. 15/316,978, filed Aug. 13, 2014, which is the U.S. National Phase under 35 U.S.C. § 371 of International Application No. PCT/GB2015/051671, filed Jun. 9, 2015, designating the United States and published in English on Dec. 17, 2015, as WO 2015/189585, which claims priority to United Kingdom Application No. 1410174.5, filed Jun. 9, 2014, each of which is incorporated by reference in its entirety.

FIELD

This invention relates to a process for purifying (hydro)fluoroolefins.

BACKGROUND

The listing or discussion of background information or an apparently prior-published document in this specification should not necessarily be taken as an acknowledgement that the information or document is part of the state of the art or is common general knowledge.

(Hydro)halocarbons are typically used as refrigerant or propellant materials. Over the last 20 years, the variety of (hydro)halocarbons used in these applications has changed in view of environmental concerns.

Dichlorodifluoromethane (refrigerant R-12) possesses a suitable combination of desirable refrigerant properties, and was for many years the most widely used refrigerant. Due to international concern that fully and partially halogenated chlorofluorocarbons were damaging the earth's protective ozone layer, there was general agreement that their manufacture and use should be severely restricted and eventually phased out completely. The use of dichlorodifluoromethane was phased out in the 1990's.

1,1,1,2-tetrafluoroethane (R-134a) was introduced as an alternative replacement refrigerant for R-12, particularly for mobile air-conditioning. However, despite having no significant ozone depletion potential, R-134a has a global warming potential (GWP) of 1300.

In response to this, (hydro)fluoroolefins are increasingly being considered as working fluids in applications such as refrigeration, heat pumping, foam blowing, propellants and flame retardants. 2,3,3,3-tetrafluoropropene (R-1234yf), which has a GWP of 4, has been identified as a candidate alternative refrigerant to replace R-134a in certain applications, notably in mobile air-conditioning or heat pumping applications.

As the next generation of low-GWP (hydro)fluoroolefins are adopted across a wide range of systems, mixtures of (hydro)fluoroolefins and previous refrigerants, such as R-134a, are expected to occur during the recovery and recycling of refrigerants. For example, contamination of a (hydro)fluoroolefin with R-134a may be expected when the (hydro)fluoroolefin is used in a system which previously utilised R-134a.

The comparatively higher cost and reduced availability of such (hydro)fluoroolefins makes the ability to separate such mixtures desirable. For example, in certain applications (e.g. mobile air-conditioning) it may not be tolerable or permissible to return a low-GWP component to a system if it is contaminated with significant levels of high-GWP refrigerant, i.e. R-134a.

However, the separation of such (hydro)fluoroolefins from undesired halogenated ethanes and methanes can be difficult and unattractive. For example, R-134a forms a minimum boiling azeotrope with R-1234yf, making distillation difficult. As the composition of such an azeotrope varies to some extent with system pressure, a twin column distillation system could be employed in order to separate the two components. However, such a system would be very expensive to build, and complex to operate. The use of a complex distillation system is also not an attractive option for the wider refrigerant supply chain, such as use by service contractor companies or refrigerant distributors.

The subject invention addresses the above deficiencies by providing a means for such a separation.

SUMMARY

In a first aspect, the invention provides a process for treating a composition comprising one or more desired (hydro)fluoroolefins as a major component and one or more undesired halogenated ethanes, halogenated methanes or mixtures thereof so as to reduce the concentration of at least one undesired halogenated ethane or halogenated methane, the process comprising contacting the composition with an adsorbent comprising pores having openings which have a size across their largest dimension of about 6 Å or less, for example so as to retain at least a portion of the ethanes and/or methanes in said adsorbent.

The inventors have surprisingly found that the use of an adsorbent comprising pores having openings which have a size across their largest dimension of about 6 Å or less is highly selective in retaining undesired halogenated ethanes and/or methanes compared to (hydro)fluoroolefins.

In an second aspect of the invention, there is provided a method for recovering a desired component of a spent refrigerant, the method comprising optionally removing a refrigerant from the refrigerant system and contacting the refrigerant with an adsorbent comprising pores having a size opening across their largest dimension of 6 Å or less to remove or reduce the concentration of one or more undesired components, the desired component comprising a (hydro)fluoroolefin, the undesired component comprising a halogenated ethane and/or halogenated methane, for example such that at least a portion of the ethanes and/or methanes are retained in said adsorbent.

In a third aspect of the invention, there is provided a kit for recovering a desired component of a spent refrigerant, the kit comprising an apparatus comprising an adsorbent comprising pores having a size opening across their largest dimension of 6 Å or less and instructions for removing the refrigerant from the refrigerant system and contacting the refrigerant with the apparatus to remove or reduce the concentration of one or more undesired components, the desired component comprising a (hydro)fluoroolefin, the undesired component comprising a halogenated ethane and/or halogenated methane, for example such that at least a portion of the ethanes and/or methanes are retained in said adsorbent.

DETAILED DESCRIPTION

Preferably, the desired (hydro)fluoroolefin comprises at least 10 wt %, for example at least 20 wt %, at least 30 wt %, at least 40 wt %, at least 50 wt %, at least 60 wt %, at least 70 wt %, at least 80 wt % or at least 90 wt % of the composition or refrigerant to be treated.

In some embodiments the adsorbent comprises pores having openings which have a size across their largest dimension in the range of from about 4 Å to about 6 Å.

In an embodiment the adsorbent comprises pores having openings which have a size across their largest dimension of about 5 Å.

Preferably, the adsorbent is a molecular sieve, such as a zeolite.

In a preferred embodiment the desired (hydro)fluoroolefin is a (hydro)fluoropropene, for example a tetrafluoropropene, preferably 2,3,3,3-tetrafluoropropene (R-1234yf). In other embodiments, the tetrafluoropropene may include, say, 1,3,3,3-tetrafluoropropene, preferably E-1,3,3,3-tetrafluoropropene.

In an embodiment, the at least one undesired halogenated ethane or halogenated methane is a halogenated ethane. In preferred embodiments, the halogenated ethane is a fluorinated ethane such as a tetrafluoroethane, preferably 1,1,1,2-tetrafluoroethane (R-134a).

The contacting step of the process should be conducted at a temperature that allows adsorption to occur. The process is preferably performed, at least in part, at a temperature of from about 0° C. to about 200° C., such as from about 20° C. to about 100° C. In some preferred embodiments, the process is performed, at least in part, at a temperature from about 20° C. to about 60° C., preferably at a temperature of about 40° C.

The contacting step of the process may be conducted at a pressure sufficient to keep the components of the composition in the liquid or gas phase as appropriate. In a preferred embodiment, the contacting step is conducted at a pressure of from about 0.1 MPa to the saturation pressure.

The process may further comprising an adsorbent treatment step prior to the contacting step. Such an adsorbent treatment step may comprise a heat treatment step, preferably comprising heating the adsorbent to a maximum temperature of at least 150° C., preferably at least 200° C., for example at least 300° C. or at least 400° C.

The heat treatment step may preferably comprise heating the adsorbent to the maximum temperature at a rate of from 1° C./minute to 100° C./minute, such as 10° C./minute to 60° C./minute, preferably at a rate of from 20° C./minute to 40° C./minute. In an embodiment, the heat treatment step comprises maintaining the adsorbent at or around the maximum temperature for a time of from 1 second to 1 hour.

In a further embodiment, the adsorbent treatment step comprises an exposure step comprising exposing the adsorbent to one or more inert gases, preferably $N_2$ or one or more noble gases, preferably wherein the exposure step is performed before, during or after the heat treatment step. Preferably, the exposure is performed during at least part of the heat treatment step.

The process typically removes at least 50% by weight, preferably 90% by weight, even more preferably 98% of the undesired halogenated ethanes, halogenated methanes or mixtures thereof. In some embodiments, the process reduces the concentration of the undesired halogenated ethanes, halogenated methanes or mixtures thereof to levels at, around or below the limit of detection by gas chromatography.

In an embodiment the adsorbent is dried before use, preferably to a level wherein the moisture content of the adsorbent is less than about 1.5% by weight. Alternatively, the adsorbent may be used in the form it is obtained from the manufacturer.

Typically, the process is conducted by passing the composition, at least once, through a polishing bed, such as a granulated solid sorbent bed, containing the adsorbent. In an embodiment the composition is passed through two or more polishing beds. The polishing bed may comprise a packed or fluidised bed.

It should be appreciated that a composition to be treated may be contacted with the adsorbent more than once. In such a process the composition may be subjected to repeated contacts with one or more types of adsorbent. Repeated contact will further reduce the content of undesired halogenated ethanes and/or methanes.

Typically, the composition to be treated may be contacted with the adsorbent as many times as necessary to remove a sufficient quantity of the undesired halogenated ethanes and/or methanes. The number of times that a composition is contacted with the adsorbent depends on a number of factors, such as the freshness of the adsorbent and the initial level of impurities.

The process of the invention may further comprising a step of regenerating the adsorbent after it has been contacted with the composition.

The regeneration step may be carried out through the use of a temperature change. In such a regeneration step, the adsorbent may be regenerated by raising the temperature of the adsorbent and purging it with a hot inert gas, typically the gas will be passed in an opposite direction to that of the composition. It will be appreciated that such a regeneration step must provide sufficient energy to raise the vessel, adsorbent and adsorbate to the desorption temperature, provide the heat of desorption and (if necessary) raise the adsorbent and the vessel to the regeneration temperature.

The regeneration step may comprise subjecting the adsorbent to a change in pressure. In such a regeneration step, the adsorbent may be regenerated by reducing the partial pressure of the adsorbate. This can be achieved by reducing the total pressure of the system, introducing an inert gas while total system pressure is maintained, or a combination of the two.

If desired, the process may further comprise one or more additional purifying steps, which may be conducted before and/or after the contacting step. Such an additional step may comprise the use of one or more molecular sieves, preferably wherein the one or more molecular sieves are acid stable. The additional purifying steps may comprise the use of drying agents and/or distillation techniques.

The process of the invention is carried out, at least in part, in the gas or liquid phase.

The present invention is now illustrated, but not limited by, the following description and Examples, with reference to the following drawings:

FIG. 1 shows a chart representing the 2 hour absorption capacity of a range of absorbent materials for each of the refrigerants R-134a, 1234yf and E-1234ze;

FIG. 2 shows a chart representing the heat of absorption for a range of absorbent materials for each of the refrigerants R-134a, 1234yf and E-1234ze.

As described above, the invention provides a method for the separation of one or more undesired halogenated ethanes and/or methanes from a composition comprising one or more desired (hydro)fluoroolefins as a major component. Such a method serves to reduce the concentration of at least one undesired halogenated ethane or halogenated methane through the retention by the absorbent of at least a portion of the halogenated ethanes and/or methanes. The process comprises contacting the composition with an adsorbent comprising pores having openings across their largest dimension of about 6 Å or less, preferably between 4 Å and 6 Å, (also referred to as 'nominal pore diameter').

A particularly preferred variety of adsorbent is a zeolite molecular sieve material preferably having a pore size across its largest dimension of approximately 5 Å, however alternative molecular sieve materials having similar pore dimensions may also be effective.

The use of such an adsorbent is unexpectedly selective in retaining, within the adsorbent, undesired halogenated ethanes and/or methanes from a composition comprising desired (hydro)fluoroolefins as a major component.

A composition to be treated may be contacted with a granulated solid sorbent bed comprising the adsorbent. Such a contacting step may be conducted as part of a "once through" process, wherein the product composition is recovered after being contacted with the adsorbent.

Alternatively, the composition to be treated may be contacted with a single granulated solid sorbent bed, comprising the adsorbent, multiple times as part of a cyclic process. In which case the sorbent may be regenerated through a change in temperature or pressure as described above, prior to the composition being re-contacted.

Twin or multi sorbent bed schemes may also be adopted in order to work the process. In two or multi bed schemes, one or more temperature changes as described above may be employed in order to regenerate the sorbent after each time the composition has been contacted with the sorbent bed. Such processes are known also as "temperature-swing processes". For example, in a two bed temperature swing process, the second bed becomes operational while the first is regenerated, and vice-versa. It will be appreciated that for the process to be continuous, the regeneration time will be equal to the adsorption time so that the composition feed stream can be switched between the beds.

Alternatively, in a two or multi bed scheme, one or more pressure changes, as described above, may be employed to regenerate the sorbent after each contacting step, known also as "pressure-swing" processes. Similarly to temperature swing processes, the composition feed may be switched between beds. As pressure changes can typically be effected more quickly than temperature changes, cycle times can be significantly quicker than temperature swing processes.

The process of the invention may be used in preparative chromatographic separation processes.

The processes of invention may be used in numerous applications.

The invention may be employed as part of the synthesis and/or purification of desired (hydro)fluoroolefins, in order to remove unwanted by-products or impurities, such as halogenated ethanes and/or halogenated methanes that could be present in the final product.

Alternatively, the invention may be employed in order to recover and/or purify a refrigerant that has been used in a system to replace an undesired halogenated ethane or methane refrigerant.

Where the invention is used to recover and/or purify a refrigerant as previously discussed, the invention may be used in situ in the refrigeration apparatus, e.g. a mobile air-conditioning unit. Alternatively, the invention may be operated in a separate apparatus in which the composition to be treated is introduced to the apparatus.

The invention may also form part of a kit for recovering a desired component of a spent refrigerant in which the kit comprises an apparatus comprising an adsorbent comprising pores having a size opening across their largest dimension of 6 Å or less, and instructions for removing the refrigerant from the refrigerant system and contacting the refrigerant with the apparatus to remove or reduce the concentration of one or more undesired components.

In a further aspect, the invention provides a heat transfer fluid comprising at least one desired (hydro)fluoroolefin as described above and being substantially free of any undesired halogenated methanes or ethanes, the at least one (hydro)fluoroolefin having been purified by a method as described above.

In another aspect, the invention provides a heat transfer device comprising a heat transfer fluid comprising one or more desired (hydro)fluoroolefins and an adsorbent comprising pores having openings which have a size across their largest dimension of about 6 Å or less. Preferably, the heat transfer device is a refrigeration system.

EXAMPLES

In the following Examples, industrial grade R-1234yf and R-134a was obtained from Apollo Scientific limited and Mexichem. The adsorbents were obtained from Aldrich and Chemviron.

Examples 1 to 10

The uptake of gas phase adsorbates by adsorbents in real time was measured by TGA analyser. The following adsorbents were tested:

Molecular sieve 3A—pores having openings which have a size across their largest dimension of about 3 Å;

Molecular sieve 4A—pores having openings which have a size across their largest dimension of about 4 Å;

Molecular sieve 5A—pores having openings which have a size across their largest dimension of about 5 Å;

Molecular sieve 13X—pores having openings which have a size across their largest dimension of about 10 Å;

and Chemviron 207ea activated charcoal.

A small sample (approximately 50 mg) of each adsorbent was accurately weighed into a 100 μL aluminium crucible before being loaded into the TGA furnace.

The adsorbent was first pre-treated by being equilibrated at 30° C. under nitrogen (75 mL/min) for 5 minutes, before being heated to 450° C. at 30° C./minute under flowing nitrogen (75 mL/min). The sample was held at 450° C. for 5 minutes, before being cooled to 40° C. at a rate of 30° C./minute, and being equilibrated at 40° C. for 5 minutes, all under a flow of nitrogen (75 mL/min).

The adsorbents were then exposed to 3.3% v/v refrigerant (R-1234yf or R-134a) in nitrogen (75 mL/min), at 40° C. for 120 minutes.

The results are shown in Table 1, with FIGS. 1 and 2 illustrating the capacity of the adsorbents and the heat of adsorption in each case.

As can be seen from the Table and Figures, adsorbents comprising pores having openings which have a size across their largest dimension of below about 6 Å, particularly between 4 Å and 6 Å, show surprising selectivity for the halogenated ethane over the (hydro)fluoroolefin. This indicates the proficiency of such adsorbents for separating halogenated ethanes from (hydro)fluoroolefins.

TABLE 1

| Reference Example | Adsorbent | Adsorbate | Wt (mg) | Conc (v/v) | Drying wt loss (mg) | Dry wt (mg) | Wt gain (mg) | Capacity (% wt) | Capacity (mol/Kg) | Equilibrium | Exotherm (mj) | $\Delta H_{(ads)}$ (kj/mol) |
|---|---|---|---|---|---|---|---|---|---|---|---|---|
| 1 | 3A | 134a | 58.6 | 3.3 | 9.1937 | 49.4063 | 1.6507 | 3.34 | 0.33 | No | 137.65 | 8.5 |
| 2 | 4A | 134a | 55.8 | 3.3 | 5.3326 | 50.4674 | 2.2154 | 4.39 | 0.43 | No | 239.68 | 11 |
| 3 | 5A | 134a | 54.2 | 3.3 | 8.1745 | 46.0255 | 5.1451 | 11.18 | 1.1 | No | 330.82 | 6.6 |
| 4 | 13X | 134a | 49.7 | 3.3 | 12.2144 | 37.4856 | 12.8923 | 34.39 | 3.37 | Yes | 3447.79 | 27.3 |
| 5 | 207ea | 134a | 34.2 | 3.3 | 0.9434 | 33.2566 | 2.5564 | 7.69 | 0.75 | Yes | 339.64 | 13.6 |
| 6 | 3A | 1234yf | 56.3 | 3.3 | 9.8521 | 46.4479 | 1.9397 | 4.18 | 0.37 | No | 62.18 | 3.3 |
| 7 | 4A | 1234yf | 53.3 | 3.3 | 10.873 | 42.427 | 2.1945 | 5.17 | 0.45 | No | 72.99 | 3.4 |
| 8 | 5A | 1234yf | 59.7 | 3.3 | 11.0719 | 48.6281 | 2.3742 | 4.88 | 0.43 | No | 88.19 | 3.8 |
| 9 | 13X | 1234yf | 47.1 | 3.3 | 11.726 | 35.374 | 10.4077 | 29.42 | 2.58 | Yes | 1821.33 | 17.8 |
| 10 | 207ea | 1234yf | 31.8 | 3.3 | 0.9976 | 30.8024 | 4.6035 | 14.95 | 1.31 | Yes | 699.24 | 15.5 |

Preferences and options for a given aspect, feature or parameter of the invention should, unless the context indicates otherwise, be regarded as having been disclosed in combination with any and all preferences and options for all other aspects, features and parameters of the invention.

The listing or discussion of an apparently prior-published document in this specification should not necessarily be taken as an acknowledgement that the document is part of the state of the art or is common general knowledge.

The invention claimed is:

1. A process of purifying a tetrafluoropropene composition comprising:
    contacting a composition with an adsorbent, the composition comprising at least one tetrafluoropropene and an impurity comprising a halogenated ethane, the adsorbent comprising pores having openings which have a size across their largest dimension of about 6 Å or less, so as to remove at least a portion of the halogenated ethane from the composition.

2. The process according to claim 1 wherein the at least one tetrafluoropropene comprises at least 10 wt % of the composition to be treated.

3. The process according to claim 1 wherein the adsorbent comprises pores having openings which have a size across their largest dimension of from about 4 Å to about 6 Å.

4. The process according to claim 1 wherein the adsorbent is a molecular sieve.

5. The process according to claim 1 wherein the adsorbent comprises a zeolite.

6. The process according to claim 1 wherein the tetrafluoropropene is 2,3,3,3-tetrafluoropropene (1234yf).

7. The process according to claim 1 wherein the halogenated ethane is a fluorinated ethane.

8. The process according to claim 7 wherein the fluorinated ethane is tetrafluoroethane.

9. The process according to claim 8 wherein the tetrafluoroethane is 1,1,1,2-tetrafluoroethane (134a).

10. The process according to claim 1 wherein the contacting step is performed, at least in part, at a temperature of from about 0° C. to about 200° C.

11. The process according to claim 1 wherein the contacting step is conducted at a pressure of from about 0.1 MPa to the saturation pressure.

12. The process according to claim 11 wherein the adsorbent treatment step comprises an exposure step comprising exposing the adsorbent to one or more inert gases.

13. The process according to claim 1 further comprising an adsorbent treatment step prior to the contacting step.

14. The process according to claim 13 wherein the adsorbent treatment step comprises a heat treatment step comprising heating the adsorbent to a maximum temperature of at least 150° C.

15. The process according to claim 14 wherein the heat treatment step comprises heating the adsorbent to the maximum temperature at a rate of from 1° C./minute to 100° C./minute.

16. The process according to claim 14 wherein the heat treatment step comprises maintaining the adsorbent at or around the maximum temperature for a time of from 1 second to 1 hour.

17. The process according to claim 1 wherein the process removes at least 50% by weight of the halogenated ethane.

18. The process according to claim 17 wherein the process reduces the concentration of the halogenated ethane to levels at, around or below the limit of detection by gas chromatography.

19. The process according to claim 1 wherein the adsorbent is dried before use.

20. The process according to claim 1 further comprising a step of regenerating the adsorbent after it has been contacted with the composition.

21. The process according to claim 20 wherein the regenerating step comprises contacting the adsorbent with a heated stream of inert gas and/or heating the adsorbent whilst the or an inert gas is passed over it.

22. The process according to claim 20 wherein the regenerating step comprises subjecting the adsorbent to a change in pressure.

23. The process according to claim 1 further comprising one or more additional purifying steps, which may be conducted before and/or after the contacting step.

24. The process according to claim 1 which is carried out, at least in part, in the gas or liquid phase.

25. A process for treating a composition comprising one or more desired tetrafluoropropenes and one or more undesired halogenated ethanes, so as to reduce the concentration of at least one undesired halogenated ethane, the process comprising contacting the composition with an adsorbent comprising pores having openings which have a size across their largest dimension of about 6 Å or less, wherein the moisture content of the adsorbent is less than about 1.5% by weight.

26. A method for recovering a desired component of a spent refrigerant, the method comprising removing a spent refrigerant comprising a desired component and an undesired component from a refrigerant system and contacting the spent refrigerant with an adsorbent comprising pores having a size opening across their largest dimension of 6 Å or less to remove or reduce the concentration of one or more undesired components, the desired component comprising a tetrafluoropropene, the undesired component comprising a halogenated ethane.

27. The method according to claim 26 wherein the tetrafluoropropene comprises at least 10 wt % of the spent refrigerant.

28. A kit for recovering a desired component of a spent refrigerant, the kit comprising an apparatus comprising an adsorbent comprising pores having a size opening across their largest dimension of 6 Å or less and instructions for removing a spent refrigerant comprising a desired component and an undesired component from a refrigerant system and contacting the spent refrigerant with the apparatus to remove or reduce the concentration of one or more undesired components, the desired component comprising a tetrafluoropropene, the undesired component comprising a halogenated ethane.

* * * * *

UNITED STATES PATENT AND TRADEMARK OFFICE
CERTIFICATE OF CORRECTION

PATENT NO. : 11,007,471 B2  
APPLICATION NO. : 16/588802  
DATED : May 18, 2021  
INVENTOR(S) : Andrew Sharratt et al.

It is certified that error appears in the above-identified patent and that said Letters Patent is hereby corrected as shown below:

On the Title Page

In (73) Assignee, second line, delete "Tlalnepantla" and insert in its place --San Luis Potosi C.P.--.

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*